United States Patent
Harang

[11] Patent Number: 6,110,478
[45] Date of Patent: Aug. 29, 2000

[54] COMPOSITION HAVING TANNING AND PHOTOPROTECTIVE ACTIVITY, AND ITS COSMETIC APPLICATIONS

[75] Inventor: Benoît Harang, Sevres, France

[73] Assignee: Laboratoire Oenobiol, Paris, France

[21] Appl. No.: 09/202,324

[22] PCT Filed: Jun. 12, 1997

[86] PCT No.: PCT/FR97/01052

§ 371 Date: Mar. 4, 1999

§ 102(e) Date: Mar. 4, 1999

[87] PCT Pub. No.: WO97/47278

PCT Pub. Date: Dec. 18, 1997

[30] Foreign Application Priority Data

Jun. 12, 1996 [FR] France .................................. 96 07279
Jan. 7, 1997 [FR] France .................................. 97 00082

[51] Int. Cl.$^7$ ...................................................... A61K 7/40
[52] U.S. Cl. ............................. 424/401; 424/59; 514/725
[58] Field of Search ..................... 424/401, 59; 514/725

[56] References Cited

U.S. PATENT DOCUMENTS 5,290,605  3/1994  Shapira .

FOREIGN PATENT DOCUMENTS

2 100 886   3/1972  France .
274 235     7/1994  United Kingdom .
WO 85 03226 8/1985  WIPO .
WO 94 06310 3/1994  WIPO .

Primary Examiner—S. Mark Clardy
Assistant Examiner—Michael A. Williamson
Attorney, Agent, or Firm—Morgan, Lewis and Bockius, LLP

[57] ABSTRACT

An oral or topical composition having tanning and sunscreening activity, and the cosmetic uses thereof, are disclosed. The composition regulates skin pigmentation and includes carotenoids. Said composition essentially contains a component (a) consisting of at least one natural carotenoid having provitamin A activity, and selected from the group which consists of β-carotene and/or α-carotene, and a component (b) corresponding to at least one natural carotenoid having no provitamin A activity, and consisting of lycopene, optionally in combination with a further component (b) selected from the group which consists of zeaxanthine, cryptoxanthine and lutein or a mixture thereof. The ratio of components (a) to lycopene is from 0.95:1 to 1:50.

16 Claims, 4 Drawing Sheets

COMPOSITION HAVING TANNING AND PHOTOPROTECTIVE ACTIVITY, AND ITS COSMETIC APPLICATIONS

FIELD OF THE INVENTION

The present invention relates to a composition having tanning and photoprotective activity intended to be administered either by the oral route, or by topical application, as well as to its cosmetic applications.

BACKGROUND

The cutaneous pigmentation of mammals in general, and of man in particular, is based on the biosynthesis of a nitrogenous pigment, melanin, from tyrosine, whose regulation is under the influence of several parameters:

tyrosinase, produced by the pigment cell, the melanocyte, which under the influence of ultraviolet light catalyses the oxidation of tyrosine to dihydroxyphenylalanine (DOPA), then to dihydroxyindole and finally to melanin, the melanin can then be subjected to oxidative polymerizations which will accentuate its coloration; this pigment is present in the form of organelles, the melanosomes, in the dendrites of the abovementioned melanocytes and these melanosomes are then transmitted to the keratinocytes, which transport the melanin to the surface of the skin where it is progressively eliminated during natural desquamation.

The melanin formed is composed of two types, (1) eumelanin, which is a black-brown color and is formed by polymerization of oxidation products of dopaquinone and (2) pheomelanin which is a reddish-brown color and is formed by polymerization of sulfur derivatives of dopaquinone; only the first type has a photoprotective effect.

The color of the skin and its intensity thus depend on the melanin content of the keratinocytes, on the type of melanin present in these keratinocytes, on the rate of desquamation and on the thickness of the horny layer which is the layer containing the most pigment.

Essentially for cosmetic reasons, man exposes himself more and more to the sun, in order to have a tanned skin.

However, ultraviolet radiation (UVA and UVB), usually proposed for tanning (sunlamps, for example), have short term as well as long term dangers.

In addition, because of a progressive decrease in the ozone layer, the deleterious effects of ultraviolet solar radiation require the photoprotection of individuals to be increased.

To combat the harmful short-term effects of ultraviolet radiation, namely solar erythema and photosensitization, it is necessary to protect the skin.

However, all of the products for oral administration proposed in the prior art are uniquely centered on the cosmetic effect: obtainment of a "tanned" skin, and comprise the administration of β-carotene at doses clearly higher than those recommended in EEC Directive 90/496, namely 800 μg/day, expressed as vitamin A, or 6 mg of β-carotene/day.

At the doses usually used in these products from the prior art, that is to say of the order of 12 to 30 mg/day, there is accumulation of β-carotene in the keratinocytes, which gives the skin an appearance of "tanning", but does not allow it to have, in addition, active photoprotection by induction of eumelanin, during subsequent exposure to the sun.

Consequently, the Applicant has especially aimed at providing a composition which can be administered by the oral route and which responds better to the needs of practice than the compositions of the prior art, especially in that:

it has a tanning power at daily doses of β-carotene significantly lower than those used earlier to this effect and not exceeding the limits recommended in the abovementioned Directive, and it has, at the same time, a tanning power and an active photoprotective effect on account of the fact that it especially induces the production of eumelanin.

The present invention relates to a composition for cosmetic purposes, which is a regulator of cutaneous pigmentation and is adapted both to administration by the oral route and to application on the skin, of the type comprising carotenoids, characterized in that it essentially comprises a component (a) formed of at least one carotenoid of natural origin with provitamin A activity selected from the group consisting of β-carotene and α-carotene or a mixture of these, and a component (b), corresponding to at least one carotenoid of natural origin without provitamin A activity, formed by lycopene, optionally associated with another component (b), selected from the group consisting of zeaxanthin, cryptoxanthin and lutein or a mixture of these, the components (a) and the lycopene being in a ratio of between 0.95:1 and 1:50.

Pigmentation regulator, in the sense of the present invention, is understood as meaning an active principle having tanning power, that is to say inducing the endogenous synthesis of melanins.

Surprisingly, at ratios of components (a):lycopene lower than 1, both the composition intended for administration by the oral route and the composition intended to be applied on the skin have a tanning power without exposure to the sun and a photoprotective effect, during subsequent exposure to the sun.

Although the Applicant has found, surprisingly, that the composition intended for administration by the oral route, at daily doses of β-carotene significantly lower than those used previously, has a tanning power and a photoprotective effect when said (a)/lycopene ratio is lower than 1 and preferably of between 0.95:1 and 1:50, there is no limitation of doses for the compositions fit to be applied by the topical route, which comprise the same components (a) and lycopene, in the same ratios as those defined for the compositions administered by the oral route.

SUMMARY OF THE INVENTION

According to an advantageous embodiment of said composition, the component (a) is selected from the group consisting of β-carotene and α-carotene or a mixture of these.

According to another advantageous embodiment of said composition, when it is intended to be administered by the oral route, said composition comprises the component (a) in a dose lower than or equal to 800 μg, expressed as vitamin A, preferably at a dose of 400 μg, expressed as vitamin A. [→a little less than 3 mg of component (a)].

According to another advantageous embodiment of said composition, the component (b) is selected from the group consisting of zeaxanthin, cryptoxanthin, lutein and lycopene or a mixture of these.

According to an advantageous arrangement of this embodiment, the component (b) comprises lycopene at a dose of between 1 and 3 mg.

According to another advantageous embodiment of said composition it additionally comprises vitamins and/or trace elements.

Such compositions have a significant tan-inducing effect (increase in the endogenous synthesis of melanins) without causing carotenoid pigmentation and equally have a photo-protective efficacy (solar erythema).

According to another advantageous embodiment of said composition it additionally comprises at least one appropriate excipient, adapted either to oral administration, or to topical application.

According to another advantageous embodiment of said composition, it is present in the form of soft capsules.

Preferably, to obtain the sought cosmetic effect, such a composition is administered at a rate of 2 units/day.

According to another advantageous embodiment of said composition, it is in the form of cream, of lotion, of liposomes or of gel.

BRIEF DESCRIPTION OF THE DRAWING FIGURES

In addition to the preceding arrangements, the invention also comprises other arrangements, which will emerge from the description which will follow, which refers to examples of carrying out the process which is the subject of the present invention as well as to the attached drawings, in which:

FIGS. 2, 3 and 4 illustrate the evolution of the erythema after oral administration of a composition according to the invention (component (a) [β-carotene or B] 2.86 mg and component (b) [lycopene or L]: 3 mg), referred to below as composition B3/L3 compared with a composition comprising 13 mg of component (a) and 2 mg of component (b), referred to as B13/L2; FIG. 2 comprises the time in weeks on the abscissa and the variation of the oxidized hemoglobin (HbO) with and without erythema, in mg/ml, on the ordinate; FIG. 3 comprises the time in weeks on the abscissa and the variation in hemoglobin (Hb) with and without erythema, in mg/ml, on the ordinate and FIG. 4 comprises the time in weeks on the abscissa and the variation of $O_2$ with and without erythema, in mg/ml, on the ordinate.

DETAILED DESCRIPTION

It must be well understood, however, that these examples are given uniquely by way of illustration of the subject of the invention, of which they are not in any way a limitation.

EXAMPLE 1

Preparation of a Composition for Oral Administration According to the Invention

| Soft capsules containing: | |
| --- | --- |
| | B3/L3 |
| Excipients: | |
| Hydrogenated soybean oil | 40 mg |
| Wheat oil | 95 mg |
| Soybean lecithin | 20 mg |
| Vitamins: | |
| Natural tocopherols | 5 mg |
| Ascorbic acid | 30 mg |
| Component (a): | |
| 20% betatene | 15 mg[1] |
| Component (b): | |
| 5% lycopene | 60 mg[2] |
| A suspension of 20% betatene comprises 200 mg/g of carotenoids divided as follows: | |
| β-carotene | 190.5 |
| α-carotene | 6 |
| zeaxanthin | 1.2 |
| cryptoxanthin | 1.4 |
| lutein | 0.9 |

[1]Corresponding to 2.86 mg of component (a) and [2]corresponding to 3 mg of lycopene.

EXAMPLE 2

Study of the Tanning Effect and of the Photoprotective Effect of the Composition According to Example 1 (Referred to as B3/L3)

Comparison with a Composition Comprising 13 mg of Carotenoids Having Provitamin A Activity and 2 mg of Lycopene (Referred to as B13/L2)

The study is a single-center, double-blind, randomized 8-week study of a B3/L3 composition according to the invention according to Example 1 and of a B13/L2 composition comprising 13 mg of carotenoids having provitamin A β-carotene activity, including a total of 20 subjects. This study was carried out in Germany, in winter.

DETAILS OF THE STUDY

The subjects are selected after a medical examination intended to verify their general good state of health.

Regular visits are necessary to verify tolerance and to carry out the evaluation of:

exposure to UV chromametric measurements of the value of b (yellow), L (luminescence) and a (red)

direct determination by multiple reflection spectrometry of: hemoglobin, oxidized hemoglobin, oxygen, melanins and β-carotene.

The efficacy is determined by a significant improvement in these parameters by comparing them with the results obtained on the day of randomization, before taking the composition.

The dose-response relationship is evaluated by the determination of the number of responders in each group.

| DESCRIPTION OF THE STUDY | | | | | |
|---|---|---|---|---|---|
| Day | D-28 | D0 | D7 | D14 | D28 |
| Visit number | V1 | V2V3 | V4V5 | V6V7 | V8V9 |
| Clinical examination | * | * | * | * | * |
| Exposure to UV | * | * | * | * | * |
| Chromametry | * | * | * | * | * |
| Spectrometry | * | * | * | * | * |
| Agreed consent | * | | | | |
| Randomization | * | | | | |
| Supply of the nutritional composition to be tested | * | * | * | * | * |
| Undesirable events | * | * | * | * | * |

The composition B13/L2 consists of soft capsules having the following formula:

| | B13/L2 |
|---|---|
| Hydrogenated soybean oil | 40 mg |
| Wheat oil | 95 mg |
| Soybean lecithin | 20 mg |
| Natural tocopherols | 5 mg |
| Ascorbic acid | 30 mg |
| 20% betatene | 65 mg[1] |
| 5% lycopene | 40 mg[2] |

[1] Corresponding to 12.42 mg of carotenoids having pro-vitamin A activity and
[2] corresponding to 2 mg of lycopene.

The daily treatment is one of the following:

2 capsules of B13/L2 or 2 capsules of B3/L3, at a rate of 2 capsules a day between 7 and 9 a.m. with breakfast.

Figure 1:
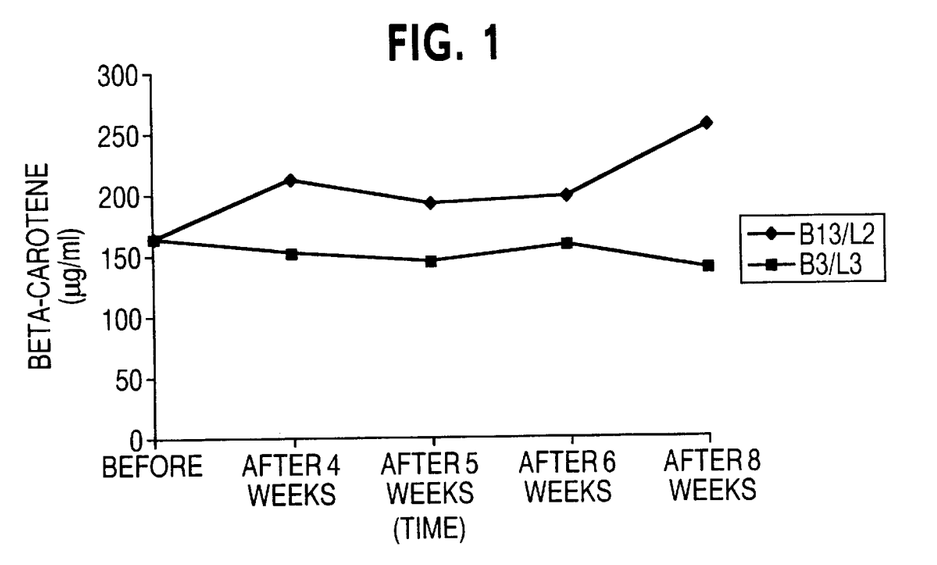
FIG. 1 illustrates the variation of β-carotene in the skin after oral administration of a composition according to the invention (component (a) [β-carotene or B] 2.86 mg and component (b) [lycopene or L]: 3 mg), referred to below as composition B3/L3, compared with a composition comprising 13 mg of component (a) and 2 mg of component (b), referred to as B13/L2; this figure has the time in weeks on the abscissa and the concentration of β-carotene in the skin in $\mu$g/ml on the ordinate.
Figure 2:
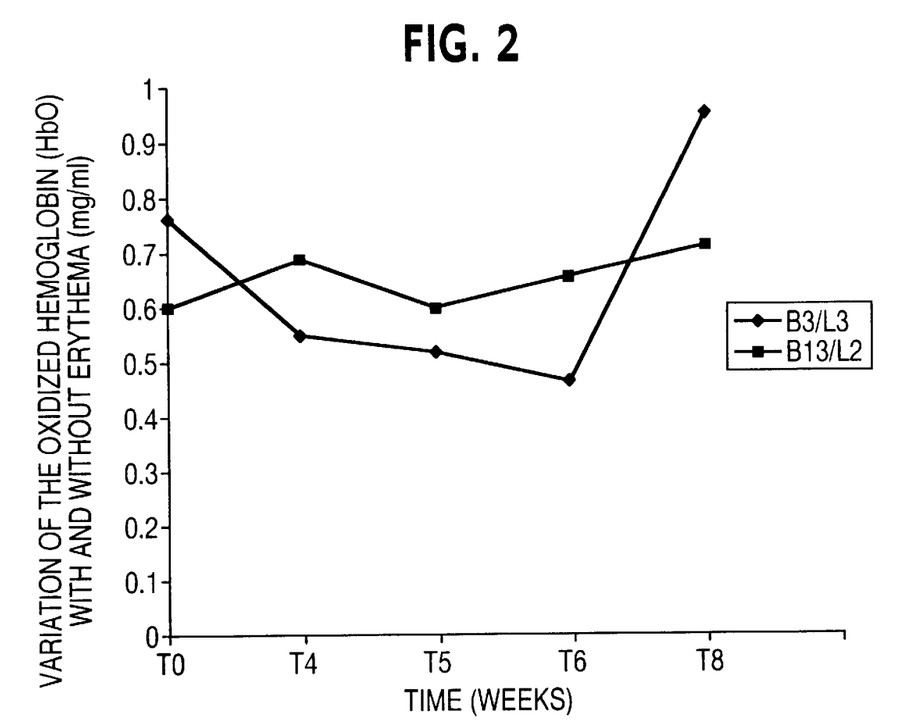
Figure 3:
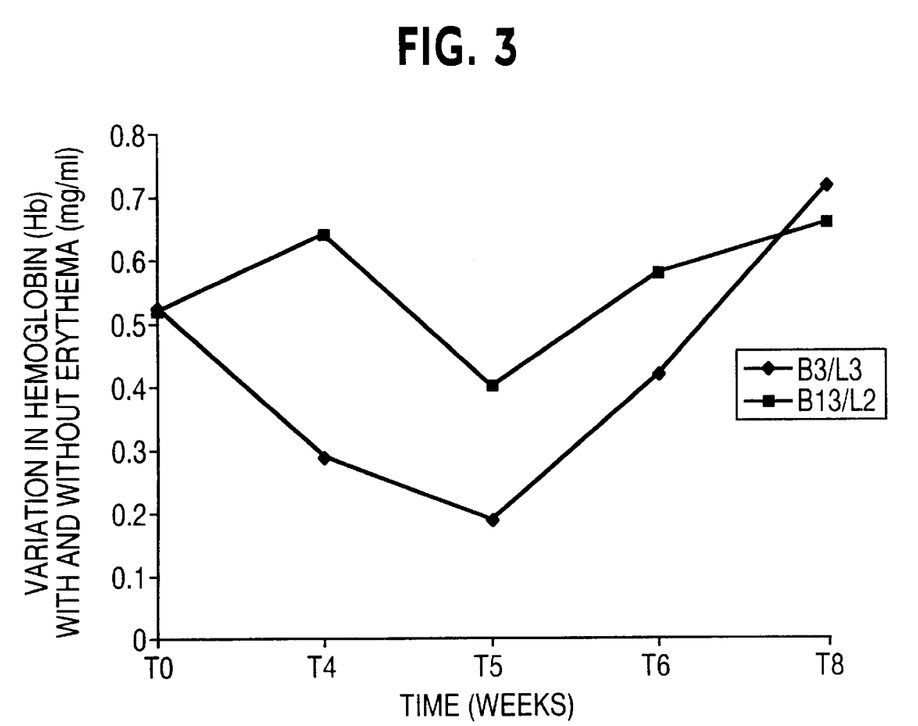
Figure 4:
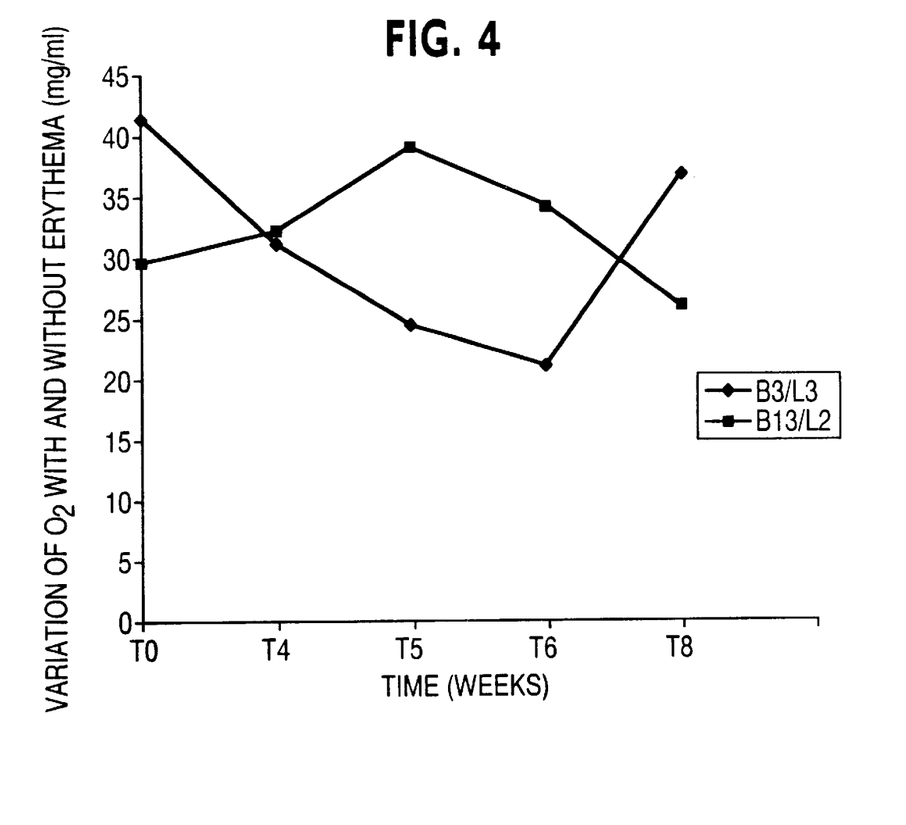

Results:

The results obtained are illustrated in Tables I to V below and in FIGS. 1 to 4 and show that the decrease in β-carotene in a composition according to the invention, with respect to the compositions of the prior art, gives a significant decrease in the erythema obtained after UV irradiation (Table III and FIG. 2: evaluation of the erythema by measurement of variations of HbO, Table IV and FIG. 3: evaluation of the erythema by measurement of variations of Hb and Table V and FIG. 4: evaluation of the erythema by measurement of variations of $O_2$), which, surprisingly, it was not possible to obtain with a high concentration of β-carotene; in addition, Tables I and II show that a composition according to the invention effectively gives a significant increase in tanning by endogenous synthesis of melanins without carotenoid pigmentation.

TABLE I

MELANIN (MEAN FOREHEAD, INTERNAL AND EXTERNAL FACE OF THE HAND, INTERNAL FACE FOREARM AND BACK) MG/ML

| | BEFORE | AFTER 4 WEEKS | AFTER 5 WEEKS | AFTER 6 WEEKS | AFTER 8 WEEKS |
|---|---|---|---|---|---|
| B13/L2 | | | | | |
| Subject 1 | 0.57 | 0.59 | 0.66 | 0.60 | 0.61 |
| Subject 5 | 0.56 | 0.61 | 0.61 | 0.60 | 0.63 |
| Subject 6 | 0.59 | 0.64 | 0.67 | 0.64 | 0.64 |
| Subject 8 | 0.62 | 0.66 | 0.66 | 0.65 | 0.65 |
| Subject 10 | 0.62 | 0.65 | 0.66 | 0.69 | 0.63 |
| Subject 11 | 0.65 | 0.71 | 0.70 | 0.72 | 0.68 |
| Subject 12 | 0.64 | 0.71 | 0.69 | 0.74 | 0.70 |
| Subject 15 | 0.62 | 0.65 | 0.63 | 0.68 | 0.65 |
| Subject 16 | 0.58 | 0.63 | 0.62 | 0.63 | 0.60 |
| Subject 19 | 0.57 | 0.63 | 0.61 | 0.63 | 0.64 |
| Mean | 0.60 | 0.65 | 0.65 | 0.66 | 0.64 |
| SD | 0.03 | 0.04 | 0.03 | 0.05 | 0.03 |
| B3/L3 | | | | | |
| Subject 2 | 0.58 | 0.63 | 0.62 | 0.64 | 0.61 |
| Subject 3 | 0.68 | 0.66 | 0.66 | 0.65 | 0.64 |
| Subject 4 | 0.58 | 0.63 | 0.63 | 0.62 | 0.63 |
| Subject 7 | 0.65 | 0.70 | 0.70 | 0.65 | 0.64 |
| Subject 9 | 0.63 | 0.67 | 0.66 | 0.70 | 0.67 |
| Subject 13 | 0.62 | 0.70 | 0.65 | 0.70 | ND |
| Subject 14 | 0.62 | 0.64 | 0.63 | 0.66 | 0.67 |
| Subject 17 | 0.63 | 0.67 | 0.67 | 0.68 | 0.68 |
| Subject 18 | 0.61 | 0.67 | 0.64 | 0.66 | 0.64 |
| Subject 20 | 0.59 | 0.58 | 0.61 | 0.59 | 0.61 |
| Mean | 0.62 | 0.66 | 0.65 | 0.66 | 0.64 |
| SD | 0.03 | 0.04 | 0.03 | 0.03 | 0.03 |

TABLE II

| | CONCENTRATIONS OF BETA-CAROTENE IN THE SKIN | | | | |
|---|---|---|---|---|---|
| | BEFORE | AFTER 4 WEEKS | AFTER 5 WEEKS | AFTER 6 WEEKS | AFTER 8 WEEKS |
| B13/L2 | | | | | |
| Back with erythema | 184.76 | 238.08 | 208.97 | 224.24 | 296.57 |
| Back without erythema | 73.21 | 161.26 | 116.28 | 101.51 | 148.13 |
| Internal face of the forearm | 55.59 | 85.42 | 73.28 | 73.49 | 84.4 |
| External face of the hand | 76.61 | 139.54 | 70.91 | 110.23 | 120.41 |
| Internal face of the hand | 348.1 | 329.27 | 240.24 | 346.42 | 437.09 |
| Forehead | 237.91 | 314.92 | 438.57 | 329.26 | 447.82 |
| Mean | 162.70 | 211.42 | 191.38 | 197.53 | 255.74 |
| B3/L3 | | | | | |
| Back with erythema | 266.2 | 222.96 | 192.99 | 228.88 | 285.8 |
| Back without erythema | 126.58 | 91.07 | 92.23 | 125.68 | 106.15 |
| Internal face of the forearm | 52.5 | 49.5 | 17.76 | 40.95 | 23.8 |
| External face of the hand | 70.1 | 112.54 | 53.24 | 108.68 | 84.88 |
| Internal face of the hand | 223.61 | 261.66 | 245.78 | 257.25 | 126.75 |
| Forearm | 239.5 | 177.61 | 260.3 | 180.91 | 195.16 |
| Mean | 163.08 | 152.56 | 143.72 | 157.06 | 137.09 |

TABLE III

| | HbO (BACK WITH ERYTHEMA) − HbO (BACK WITHOUT ERYTHEMA) | | | | | | |
|---|---|---|---|---|---|---|---|
| | BEFORE | AFTER 4 WEEKS | AFTER 5 WEEKS | AFTER 6 WEEKS | AFTER 8 WEEKS | MEAN (n = 5) | MEAN (n = 4) |
| B13/L2 | | | | | | | |
| Subject 1 | 0.93 | 0.66 | 1.21 | −0.23 | 0.14 | 0.54 | 0.45 |
| Subject 5 | 1.41 | 2.12 | 0.38 | 0.1 | 1.46 | 1.09 | 0.99 |
| Subject 6 | −0.14 | 0.28 | 1.03 | 0.44 | 1.03 | 0.53 | 0.70 |
| Subject 8 | 0.34 | 0.55 | 0.04 | 0.91 | 0.16 | 0.40 | 0.42 |
| Subject 10 | 0.69 | 1.26 | 1.14 | 1.32 | 0.89 | 1.06 | 1.15 |
| Subject 11 | 0.8 | 0.68 | 0.72 | 0.83 | 1.47 | 0.9 | 0.93 |
| Subject 12 | 1.68 | −0.01 | −0.29 | 0.98 | 0.59 | 0.59 | 0.32 |
| Subject 15 | 0.34 | 0.03 | 1.3 | 0.63 | 0.42 | 0.54 | 0.60 |
| Subject 16 | 0.04 | 0.26 | 0.12 | 0.31 | −0.1 | 0.13 | 0.15 |
| Subject 19 | −0.09 | 1.09 | 0.3 | 1.27 | 1.16 | 0.75 | 0.96 |
| Mean | 0.6 | 0.69 | 0.60 | 0.66 | 0.72 | 0.65 | 0.67 |
| SD | 0.62 | 0.65 | 0.56 | 0.50 | 0.56 | | |
| B3/L3 | | | | | | | |
| Subject 2 | 0.25 | 0.58 | −0.18 | 1.28 | 1.17 | 0.62 | 0.71 |
| Subject 3 | 0.08 | 0.19 | 1.09 | 0.04 | 0.31 | 0.34 | 0.41 |
| Subject 4 | 0.52 | −0.08 | 0.42 | 0.54 | 0.75 | 0.43 | 0.41 |
| Subject 7 | 0.48 | 0.35 | 0.82 | 1.19 | 0.41 | 0.65 | 0.69 |
| Subject 9 | 1.55 | 0.21 | 0.51 | −0.06 | 2.5 | 0.94 | 0.79 |
| Subject 13 | 0.61 | −0.03 | 0.04 | 0.02 | ND | 0.16 | 0.01 |
| Subject 14 | 1.24 | −0.11 | −0.13 | −0.11 | 0.08 | 0.19 | −0.07 |
| Subject 17 | 1.18 | 1.81 | 0.1 | 0.54 | 1.02 | 0.93 | 0.87 |
| Subject 18 | 1.32 | 1.6 | 1.57 | 0.81 | 1.86 | 1.43 | 1.46 |
| Subject 20 | 0.41 | 0.98 | 1 | 0.43 | 0.55 | 0.67 | 0.74 |
| Mean | 0.76 | 0.55 | 0.52 | 0.47 | 0.96 | 0.64 | 0.60 |
| SD | 0.69 | 0.67 | 0.58 | 0.51 | 0.81 | | |

TABLE IV

Hb (BACK WITH ERYTHEMA) − Hb (BACK WITHOUT ERYTHEMA)

| | BEFORE | AFTER 4 WEEKS | AFTER 5 WEEKS | AFTER 6 WEEKS | AFTER 8 WEEKS | MEAN (n = 5) | MEAN (n = 4) |
|---|---|---|---|---|---|---|---|
| B13/L2 | | | | | | | |
| Subject 1 | 1.01 | 0.57 | 1.21 | −0.23 | 0.14 | 0.54 | 0.42 |
| Subject 5 | 1.65 | 2.4 | 0.37 | −0.07 | 0.87 | 1.21 | 1.11 |
| Subject 6 | −0.37 | −0.31 | 0.65 | 0.17 | 0.87 | 0.20 | 0.35 |
| Subject 8 | 0.37 | 0.64 | −0.21 | 0.86 | 0.32 | 0.40 | 0.40 |
| Subject 10 | 0.97 | 1.1 | 1.16 | 1.59 | 0.45 | 1.05 | 1.08 |
| Subject 11 | 0.89 | 0.67 | 0.49 | 0.81 | 1.39 | 0.85 | 0.84 |
| Subject 12 | 1.26 | 0.04 | −0.75 | 1 | 0.78 | 0.47 | 0.27 |
| Subject 15 | 0.23 | −0.08 | 1.72 | 0.56 | 0.51 | 0.59 | 0.68 |
| Subject 16 | −0.23 | 0.17 | −0.23 | −0.17 | −0.49 | −0.19 | −0.18 |
| Subject 19 | −0.55 | 1.2 | −0.37 | 1.3 | 0.97 | 0.51 | 0.78 |
| Mean | 0.523 | 0.64 | 0.404 | 0.582 | 0.666 | 0.56 | 0.57 |
| SD | 0.73 | 0.79 | 0.80 | 0.64 | 0.63 | | |
| B3/L3 | | | | | | | |
| Subject 2 | −0.07 | 0.61 | −0.37 | 0.43 | 0.87 | 0.29 | 0.39 |
| Subject 3 | −0.34 | 0.08 | 1.32 | −0.02 | 0.2 | 0.25 | 0.40 |
| Subject 4 | 0.61 | −0.84 | −0.37 | 0.56 | 0.78 | 0.15 | 0.03 |
| Subject 7 | 0.61 | 0.56 | 0.64 | 1.25 | 0.82 | 0.78 | 0.82 |
| Subject 9 | 1.61 | 9.7 | 1.05 | −0.18 | 2.5 | 2.94 | not taken into account |
| Subject 13 | 0.43 | 0.11 | 0.04 | −0.02 | ND | 0.14 | 0.04 |
| Subject 14 | 0.83 | −1.26 | −1.29 | −1.23 | 0.45 | −0.3 | −0.58 |
| Subject 17 | 0.78 | 1.8 | −0.18 | 0.55 | 0.71 | 0.73 | 0.72 |
| Subject 18 | 1.44 | 1.46 | 1.24 | 0.98 | 2.05 | 1.43 | 1.43 |
| Subject 20 | 0.46 | 0.12 | 0.67 | 0.33 | −0.08 | 0.3 | 0.26 |
| Mean | 0.53 | 0.29 | 0.19 | 0.43 | 0.72 | 0.42 | 0.39 |
| SD | 0.52 | 0.98 | 0.85 | 0.48 | 0.84 | | |

TABLE V

Oxygen (BACK WITH ERYTHEMA) − Oxygen (BACK WITHOUT ERYTHEMA)

| | BEFORE | AFTER 4 WEEKS | AFTER 5 WEEKS | AFTER 6 WEEKS | AFTER 8 WEEKS | MEAN (n = 5) | MEAN (n = 4) |
|---|---|---|---|---|---|---|---|
| B13/L2 | | | | | | | |
| Subject 1 | 52 | 34.2 | 42.7 | 27.4 | 22.8 | 35.82 | 31.78 |
| Subject 5 | 49.5 | 40.9 | 32 | 12.9 | 39.4 | 34.94 | 31.30 |
| Subject 6 | 10.1 | 41 | 49.6 | 45 | 34.9 | 36.12 | 42.63 |
| Subject 8 | 24.5 | 22.1 | 15.2 | 25 | 6.6 | 18.68 | 17.23 |
| Subject 10 | 7.9 | 49.4 | 46.6 | 27.7 | 32.5 | 32.82 | 39.05 |
| Subject 11 | 31.1 | 50 | 63.4 | ND | 40.5 | 46.25 | 51.3 |
| Subject 12 | 66.2 | 302 | −5.3 | 44.2 | 31.2 | not taken into account | not taken into account |
| Subject 15 | 46.8 | 21 | 29.3 | 64.5 | 24.2 | 37.16 | 34.75 |
| Subject 16 | 28.1 | 15.4 | 39.8 | 38.5 | 8.9 | 26.14 | 25.9 |
| Subject 19 | 17.1 | 16.3 | 34.7 | 36.1 | 31.5 | 27.14 | 25.65 |
| Mean | 29.68 | 32.26 | 39.26 | 34.64 | 26.8 | 29.15 | 33.28 |
| SD | 16.13 | 16.33 | 17.67 | 19.81 | 12.34 | | |
| B3/L3 | | | | | | | |
| Subject 2 | 57.9 | 32 | −4.4 | 38.4 | 66.3 | 38.04 | 33.08 |
| Subject 3 | 33.8 | 35.9 | 32.7 | 6.1 | 29.3 | 27.56 | 26.00 |
| Subject 4 | 42.8 | 62.7 | 32.4 | 45 | 38.1 | 44.20 | 44.55 |
| Subject 7 | 15.1 | 7.5 | 42.4 | 46.2 | 6.3 | 23.50 | 25.60 |
| Subject 9 | 41.7 | 29.7 | −2.7 | −4.4 | 38.2 | 20.50 | 15.2 |
| Subject 13 | 44.6 | −13.5 | 3.9 | −4.4 | ND | 7.65 | −4.67 |
| Subject 14 | 51.1 | 32.5 | 35.9 | −9 | 41.2 | 30.34 | 25.15 |
| Subject 17 | 56.4 | 52.4 | 15.9 | 24.9 | 28 | 35.52 | 30.3 |
| Subject 18 | 57.1 | 32.1 | 49.6 | 36.2 | 44.2 | 43.84 | 40.53 |
| Subject 20 | 12.9 | 32.1 | 49.6 | 36.2 | 45 | 35.76 | 41.48 |
| Mean | 41.34 | 31.25 | 24.85 | 21.59 | 37.40 | 30.69 | 27.72 |
| SD | 16.37 | 21.42 | 20.05 | 21.51 | 16.11 | | |

EXAMPLE 3

Preparation of a Composition for Topical Administration According to the Invention

|  | B3/L3 |
|---|---|
| Excipients: | |
| Soybean lecithin | 80 mg |
| Hydrogenated soybean oil | 40 mg |
| Ceramides | 20 mg |
| Vitamins: | |
| Natural tocopherols | 5 mg |
| Ascorbic acid | 30 mg |
| Component (a): | |
| 20% betatene | |
| Component (b): | 15 mg[1] |
| 5% lycopene | 60 mg[2] |

[1]Corresponding to 2.86 mg of component (a) and
[2]corresponding to 3 mg of lycopene.

As emerges from the text hereinabove, the invention is not limited by any means to the embodiments and modes of application which are described more explicitly; on the contrary, it embraces all the variants which can come to the mind of a person skilled in the art, without departing from the scope or the range of the present invention.

What is claimed is:

1. A topical or oral composition comprising a carotenoid having provitamin A activity selected from the group consisting of β-carotene, α-carotene and mixtures thereof; in admixture with lycopene, wherein the ratio of carotenoid having provitamin A activity to lycopene is from 0.95:1 to 1:50.

2. The composition of claim 1 further comprising a carotenoid without provitamin A activity selected from the group consisting of zeaxanthin, cryptoxanthin, lutein, and mixtures thereof.

3. The composition of claim 1 wherein the amount of lycopene is between about 1 and about 3 mg.

4. The composition as claimed in any one of claims 1–3, further comprising vitamins and/or trace elements.

5. The composition as claimed in any one of claims 1–3, wherein said carotenoid having provitamin A activity is present in an amount lower than or equal to 800 μg expressed as vitamin A.

6. The composition of claim 5, wherein said carotenoid having provitamin A activity is present in an amount lower than or equal to 400 μg expressed as vitamin A.

7. The composition of claim 5, further comprising at least one excipient appropriate for oral administration of the composition.

8. The composition of claim 7, wherein said excipient provides for formulation as a soft capsule.

9. The composition as claimed in any one of claims 1–3, further comprising at least one excipient appropriate for topical administration of the composition.

10. The composition of claim 9, wherein said excipient provides for formulation as a cream, a lotion, a liposome or a gel.

11. A method of treatment for tanning skin and providing photoprotection comprising orally administering a daily dose of an effective amount of the composition as claimed in claim 5.

12. A method of treatment for tanning skin and providing photoprotection comprising orally administering a daily dose of an effective amount of the composition as claimed in claim 7.

13. A method of treatment for tanning skin and providing photoprotection comprising topically administering an effective amount of the composition as claimed in claim 9.

14. A method of treatment for tanning skin and providing photoprotection comprising topically administering an effective amount of the composition as claimed in claim 10.

15. A method of treatment for tanning skin and providing photoprotection comprising orally administering a daily dose of an effective amount of the composition as claimed in claim 8.

16. The composition of claim 5, wherein said carotenoid having provitamin A activity is present in an amount of 400 μg expressed as vitamin A.

* * * * *